United States Patent [19]

Olah

[11] Patent Number: 4,861,923
[45] Date of Patent: Aug. 29, 1989

[54] HYDRATION OF PROPYLENE TO ISOPROPYL ALCOHOL OVER SOLID SUPERACIDIC PERFLUORINATED SULFONIC ACID CATALYSTS

[75] Inventor: George Olah, Beverly Hills, Calif.

[73] Assignee: PCUK Products Chimiques Uqine Kuhlmann, Courbevoie, France

[21] Appl. No.: 648,861

[22] Filed: Sep. 7, 1984

Related U.S. Application Data

[63] Continuation of Ser. No. 178,889, Aug. 18, 1980, abandoned.

[51] Int. Cl.$^4$ .................. C07C 29/04; C07C 31/10; C07C 31/12
[52] U.S. Cl. .................................................. 568/899
[58] Field of Search ........................................ 568/899

[56] References Cited

U.S. PATENT DOCUMENTS 4,080,391  3/1978  Tsumura et al. .................... 568/899

OTHER PUBLICATIONS

Olah et al. (R), "Science", Reprint Series, Oct. 5, 1979, vol. 206, pp. 13-20.
Olah et al. (S), "J. Org. Chem.", vol. 42, Nov. 26, 1977, pp. 4,187-4,189.

Primary Examiner—J. E. Evans
Attorney, Agent, or Firm—Pennie & Edmonds

[57] ABSTRACT

A process for the hydration of lower olefins to a corresponding alcohol by reacting the olefins with water in the presence of a solid perfluorinated sulfonic superacid catalyst.

7 Claims, No Drawings

HYDRATION OF PROPYLENE TO ISOPROPYL ALCOHOL OVER SOLID SUPERACIDIC PERFLUORINATED SULFONIC ACID CATALYSTS

This is a continuation, of application Ser. No. 178,889 filed Aug. 18, 1980, now abandoned.

FIELD OF THE INVENTION

The invention is concerned with the hydration of propylene to isopropyl alcohol over solid superacid catalysts.

BACKGROUND OF THE INVENTION

The hydration of propylene to isopropyl alcohol in sulfuric acid solution through a two-step esterification-hydrolysis process was one of the first petrochemical processes, dating back to the early 1920's.

The liquid-phase, two-step process has, however, several serious disadvantages, such as the corrosive nature of the 85% sulfuric acid necessary for the propylene esterification reaction; the necessity of diluting the acid reaction medium to promote hydrolysis and to facilitate separation of the acid from the alcohol after hydrolysis and the necessity of acid reconcentration before recycle to the esterification step of the process; and the frequent need for neuralizing the alcohol product. Consequently, the direct hydration of propylene over solid catalysts is of practical significance to overcome the above difficulties.

Considerable work has therefore been done on the development of propylene hydration scheme, which do not use sulfuric or other liquid acids. The processes which have been studied generally involve contacting the olefin and water in the presence of a suitable solid catalyst at elevated temperature and pressure to produce the desired isopropyl alcohol directly. High pressures, relatively low temperatures and high steam to propylene ratios favor conversion to the alcohol.

When the hydration catalyst is active at low temperatures, the reaction is usually conducted in the presence of a large excess of liquid water (thus under corresponding high pressure). Kaiser, Beuther, Moore and Odioso (Ind. Eng. Chemistry Product Res. and Development Vol. 1 pp 296–302 (1962)) using sulfonated styrenedivinylbenzene ion-exchange resins (such as Rohm and Haas Co. Amberlyst 15 or IR-120) studies the effects of temperature, pressure, space velocity and feed composition on conversion and selectivity. When the catalyst used is not active at lower temperatures ($<150°$ C.) vapor-phase operation is used to avoid extreme pressures. The thermodynamic equilibria prevailing at higher temperatures limits the propylene conversion to quite low levels.

Some of the reported hydration processes used supported mineral or inorganic acids in a relatively low pressure, essentially vapor phase process for propylene hydration.

Catalysts used include silicophosphoric acid (U.S. Pat. No. 2,876,266) phosphoric acid on celite (U.S. Pat. No. 2,579,601) and tungstic acid on alumina (F. J. Sanders and B. F. Dodge, Ind. Eng. Chem., 26, 208 (1934).

The conversion reported for vapor-phase operations such as over phosphoric acid impregnated on Celite brand of diatomaceous earth at 225°–250° C., 550 psig is only 3.8%.

The vapor phase, direct hydration processes eliminate the major difficulties of the two-step sulfuric acid based solution process but, so far, had the disadvantage of low per-pass conversion, which is considered to be the result of thermodynamic vapor phase equilibrium conditions. Work, consequently, was directed to the use of conditions, which permit reactants to be both in the vapor (propylene) and liquid (water) phases.

Processing with liquid water permits the direct hydration of olefins in much higher per-pass conversions than can be obtained by vapor phase operation, probably because the solubility of the product alcohol in the liquid phase water changes the thermodynamic equilibrium consideration which limit the vapor phase conversions. The catalysts which can be utilized in this mixed phase processing must then show hydrothermal stability in the presence of liquid phase water at the required reaction temperature, as well as catalytic activity. The most commonly utilized catalyst for this process known until now was tungsten oxide, although silica-alumina and supported Group VI and Group VII metals also have been reported.

Ogino ((Shokubai, Tokyo) 4, 73 (1962) J. CATAL., 8, 64 (1967)) found metal sulfate-silica gel catalysts, particularly those of Fe, Al, Cr, Cu, Zn, Co, Pd, Ni, Mn, and the like, active for the hydration of propylene. He concluded that with these catalysts, an acidity range of $H_o$ of 1.5 to $-3$ is the most suitable. However, methods used in establishing surface acidities of the catalysts based on color changes of indicator dyes must be considered unreliable. There was, thus, no clear indication available as to what to expect with high acidity solid catalysts, particularly with solid superacids.

Sulfonic cation exchange resins were also claimed as catalysts. Japan Kokai No. 77,151,106 (Chemical Abstracts 88, 169578x) discloses the use of halogenated cation exchange resins of the sulfonic acid type for the hydration of lower olefins to form the corresponding alcohols. Example 1 of this patent reports the hydration of propylene to form isopropyl alcohol over a chlorinated Amberlyst 15 sulfonated styrene-divinylbenzene copolymer. The conversion rate of propylene was reported as 14.3% and the selectivity of isopropanol as 96%. A temperature of 130° C. and a pressure of 70 atm (about 1000 psi) was needed for the reaction. The same patent also claims the use of Du Pont Nafion 501 resin, a "perfluoro vinyl ether copolymer containing sulfonic radical", as catalyst.

Example 2 describes the hydration of butene-1 with this catalyst to sec.-butanol with a 3.1% conversion. The very low conversion is not explained, but its reason is apparent when considering that the commercial Nafion 501 resin used is the potassium salt of the resin sulfonic acid and not an acid catalyst. Clearly the commercial Nafion resin, which is the potassium salt of the sulfonic acid resin used in ion-membrane applications, is unsuitable as a hydration catalyst.

SUMMARY OF THE INVENTION

This invention is based on the discovery of the ability of superacidic, solid perfluorinated sulfonic acids to effectively catalize at modest temperatures and pressure, including atmospheric pressure, the hydration of lower ($C_2$ to $C_6$) olefins, particularly that of propylene to isopropyl alcohol. These catalysts can be $C_{10}-C_{18}$ perfluorinated alkanesulfonic acids, the free acid forms of perfluorinated alkenesulfonic acid polymers, such as trifluoroethylene sulfonic acid polymers, tetrafluoroethylene-trifluoroethylenesulfonic acid copolymers or the activated free acidic forms of copolymers of perfluoroalkenesulfonic acids and perfluorovinyl ethers, such as the free acid form of the commercially available Du Pont Nafion resins (designated herein as Nafion-H). The present catalysts based on perfluorinated sulfonic acids are of extremely low or no volatility, high stability of long duration under the utlized hydration conditions, which are due to the extremely high acidity, not previously achieved by any solid catalyst systems, thus allowing high selective and efficient conversion.

DETAILED DESCRIPTION OF THE INVENTION

The temperature range for the perfluorinated sulfonic acid catalyzed hydration reaction of propylene can vary between about 120° and 180° C., the water to propylene mol ratio from 1 to 50 and the space velocity (LHSV) in a static flow reactor between about 1 and 10. Optimum conditions are found between 140° and 160° C., a water to propylene mol ratio between 2 and 10, and a space velocity between 2.5 and 5. The flow system can be atmospheric or under pressure. Modest pressures (500–1000 psi) may be advantageous to increase the per-pass isopropyl alcohol yield. The reaction is preferentially carried out over a fixed bed catalyst in the vapor-phase or as a mixed phase system. Under these conditions 15–30% conversion of propylene to isopropyl alcohol is achieved per-pass with 96 to 99% selectivity. Optimum conditions for hydration of the other lower olefins can be determined routinely.

The perfluorinated solid alkanesulfonic acids used as the catalysts of this invention can be prepared by various methods, such as for example, by the use of electrofluorination in preparing the corresponding perfluorinated alkanesulfonyl fluorides, which subsequently can be hydralyzed to the related alkanesulfonic acids, according to the JOURNAL OF THE CHEMICAL SOCIETY (London) (1947) pages 2640–2645. Alternate methods of preparation include reaction of perfluorinated alkyl iodides ($R_fI$) through their Grignard reaction with sulfur dioxide or addition of sulfonyl halides to perfluorinated olefins.

Trifluoroethylenesulfonic acid polymers can be prepared by various methods, including the hydrolysis with water and a strong base (NaOH or KOH) of trifluoroethenesulfonyl fluoride polymers, according to U.S. Pat. No. 3,041,317 (CA 58 451a). The hydrolysis results in the formation of the alkali salts of the polymeric sulfonic acid, from which the active acid form is liberated by treatment with $HNO_3$ or $H_2SO_4$.

Tetrafluoroethylene-trifluoroethylenesulfonic acid copolymers can be similarly prepared according to Brit. Pat. No. 1,184,321 (Chem. Abst. 73, 15936 V)

Commercial Du Pont Nafion brand ion membrane resins, such as Nafion 501 are perfluorinated polymers having sulfonic acid groups in the amount of about 0.01 to 5 mequiv/gram catalyst. The polymer resin is the potassium salt containing a repeating structure, which can be depicted as:

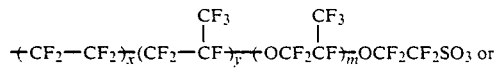

or

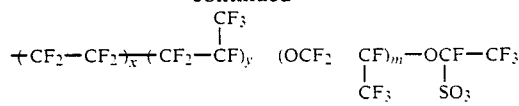

where the ratio of x over y varies from about 2 to about 50, and m is 1 or Polymers of the above structure can be prepared in various ways. One method, disclosed in Conolly et al U.S. Pat. No. 3,282,875 and Cavanaugh et al. U.S. Pat. No. 3,882,093 comprises polymerizing the corresponding perfluorinated vinyl compounds. It is also possible to prepare polymer catalyst according to U.S. Pat. No. 4,041,090 by copolymerizing the corresponding perfluorinated vinyl ethers with perfluoroethylene and/or perfluoro-alpha-olefins.

The commercial Nafion resins can be converted into their acid form (designated for differentiation as Nafion-H) by repeated treatment with aqueous strong acids, such as nitric or sulfonic acid.

A superacid is an acid having an $H_o$ value on the Hammett scale in excess of $-11$, such as $-25$. Thus, weaker acids such as sulfuric acid ($H_o$ of $-11$) or HF ($H_o$ of $-10$) are excluded.

The scope of the invention will be further described in connection with the following examples, which are set forth for purposes of illustration only and are not to be construed as limited to the scope of the invention in any manner. Although the examples utilize the preferred olified propylene, the invention is applicable to other olefins in general particularly to the lower olefins containing up to about six carbon atoms.

EXAMPLE 1

10 g of a perfluorohexadecanesulfonic acid $C_{16}F_{33}SO_3H$ was deposited via vacuum distillation on 75 g of porous chromosorb. 5 g of this catalyst was charged into a stainless steel catalytic tube reactor of $170 \times 12$ mm dimension. It was heated to 135° C. and under a pressure of 700 psig propylene (8 g/hr) and water (25 g/hr) were passed through. Isopropyl alcohol was obtained with 23% propylene conversions and 96% selectivity.

EXAMPLE 2

10 g of perfluorodecanesulfonic acid $C_{10}F_{21}SO_3H$ was deposited on 90 g of porous alumina. 5 g of this catalyst was reacted under conditions of Example 1 giving a 25% conversion of propylene to isopropyl alcohol with 97% of selectivity.

EXAMPLE 3

10 g of perfluorodecanesulfonic acid $C_{12}F_{25}SO_5H$ was used as catalyst under conditions of example 1 giving 25% conversion to isopropyl alcohol with 97% selectivity.

EXAMPLE 4

A fixed bed glass catalytic tube reactor $150 \times 8$ mm dimension was charged with 10 g of polymeric trifluoroethylenesulfonic acid catalyst. Propylene (10 g/hr) and steam (30 g/hr) were passed over the catalyst heated to 150° C. Isopropyl alcohol was obtained with 18% propylene conversion and 96% selectivity.

EXAMPLE 5

Reaction was carried out as in Example 4, but using tetrafluoroethylene-trifluoroethylenesulfonic acid polymer as catalyst. Isopropyl alcohol was obtained with 15% propylene conversion and in 98% selectivity.

EXAMPLE 6

50 g of commercial Nafion-K resin (potassium salt of the DuPont Company's ion-membrane material) was refluxed in 250 ml of deionized water for two hours. After filtering, the resin was treated with 100 ml of 20% to 25% nitric acid for 5 hours at room temperature. Filtering was followed with repeat of the nitric acid treatment three times. Finally, the resin was washed to neutrality with deionized water and dried in a vacuum drying oven at 105° C. for 24 hours. 5 g of the above activated Nafion-H catalyst was placed into a fixed bed glass catalytic tube reactor of 150×8 mm dimension. Propylene (10 g/hr) and water (30 g/hr) were passed through over the catalyst heated to 150° C. Isopropyl alcohol was obtained with a propylene conversion of 16% and a selectivity of 97%.

EXAMPLE 7

A stainless steel fixed bed catalytic reactor of 170×12 mm dimension was charged with 5 g of Nafion-H catalyst prepared as in Example 5. It was heated to 130° C. and under a pressure of 500 psig propylene (8 g/hr) and water (125 g/hr) were passed through. Isopropyl alcohol was obtained with a 31% propylene conversion and 96% selectivity.

While the invention has been described in connection with preferred embodiments, it is not intended to limit the invention to the particular forms set forth, but on the contrary, it is intended to cover such alternatives, modifications, and equivalents as may be apparent to those skilled in the art.

I claim:

1. A process for the hydration of lower olefins to a corresponding alcohol which comprises contacting said olefin and water vapor each in the gaseous phase with a solid perfluorinated alkane sulfonic acid catalyst of a $C_{10}$ to $C_{18}$ perfluorinated alkanesulfonic acid, a polymeric perfluorinated ethene sulfonic acid or a tetrafluoroethylene trifluoroethane sulfonic acid copolymer under continuous flow conditions at a reaction temperature of between about 120° and 180° C. for a sufficient time to effect hydration of the olefin to the corresponding alcohol.

2. The process according to claim 1 wherein the reaction temperature is between 140° and 160° C.

3. A process for the hydration of propylene to isopropyl alcohol which comprises contacting said propylene and water vapor each in the gaseous phase with a solid perfluorinated alkanesulfonic acid catalyst of a $C_{10}$ to $C_{18}$ perfluorinated alkanesulfonic acid, a polymeric perfluorinated ethene sulfonic acid or a tetrafluoroethylene trifluoroethane sulfonic acid copolymer under continuous flow conditions at a reaction temperature of between about 120° and 180° C. for a sufficient time to effect hydration of propylene to isopropyl alcohol.

4. The process according to claim 3 wherein the reaction temperature is between 140° and 160° C.

5. The process according to claim 3 wherein the water vapor to propylene mole ratio is between about 1 to 50.

6. The process according to claim 5 wherein the water vapor to propylene mole ratio is between about 2 to 10.

7. A process for the hydration of propylene to isopropyl alcohol which comprises contacting said propylene and water vapor in the gaseous phase with a solid $C_{10}$ to $C_{18}$ perfluorinated alkanesulfonic acid under continuous flow conditions wherein the water vapor to propylene ratio is between about 2 to 10 at a reaction temperature between about 140° and 160° C. for a sufficient time to effect hydration of propylene to isopropyl alcohol with a selectivity of at least 96%.

* * * * *